United States Patent
Ma

(10) Patent No.: US 9,784,678 B2
(45) Date of Patent: Oct. 10, 2017

(54) METHOD FOR IMPROVING FLUORESCENCE IMAGE CONTRAST

(75) Inventor: Guobin Ma, Dorval (CA)

(73) Assignee: SOFTSCAN HEALTHCARE GROUP LTD., Tortola (VG)

(*) Notice: Subject to any disclaimer, the term of this patent is extended or adjusted under 35 U.S.C. 154(b) by 1673 days.

(21) Appl. No.: 11/813,125

(22) PCT Filed: Dec. 23, 2005

(86) PCT No.: PCT/CA2005/001968
§ 371 (c)(1),
(2), (4) Date: Apr. 23, 2008

(87) PCT Pub. No.: WO2006/069444
PCT Pub. Date: Jul. 6, 2006

(65) Prior Publication Data
US 2009/0216457 A1  Aug. 27, 2009

Related U.S. Application Data

(63) Continuation-in-part of application No. 11/024,826, filed on Dec. 30, 2004, now abandoned.

(51) Int. Cl.
| | | |
|---|---|---|
| G01N 33/50 | (2006.01) | |
| G01N 21/64 | (2006.01) | |
| A61B 5/00 | (2006.01) | |
| G06T 5/00 | (2006.01) | |

(52) U.S. Cl.
CPC ....... G01N 21/6408 (2013.01); A61B 5/0059 (2013.01); G01N 21/6456 (2013.01); G06T 5/008 (2013.01); G06T 2207/10064 (2013.01); G06T 2207/30024 (2013.01)

(58) Field of Classification Search
None
See application file for complete search history.

(56) References Cited

U.S. PATENT DOCUMENTS

| | | | |
|---|---|---|---|
| 7,179,654 B2 | 2/2007 | Verdonk et al. | |
| 7,279,338 B2* | 10/2007 | Kim et al. | 436/177 |
| 2003/0175987 A1 | 9/2003 | Verdonk et al. | |
| 2006/0149479 A1* | 7/2006 | Ma | 702/19 |
| 2007/0197894 A1* | 8/2007 | Jo et al. | 600/407 |

FOREIGN PATENT DOCUMENTS

WO  9213265  8/1992

OTHER PUBLICATIONS

Neher, R. et al., "Optimizing Imaging Parameters for the Separation of Multiple Labels in a Fluorescence Image", Journal of Microscopy, vol. 213, Pt. 1, Jan. 2004, pp. 46-62.
Liljeborg, Anders et al., "Fluorescence Lifetime Imaging of Multiple Fluorophores Implemented in Confocal Microscopy", EUROPTO Conference on Optical Microscopy, Stockholm, Sweden, Sep. 1998, SPIE, vol. 3568, pp. 82-88.
Clayton, Andrew H. A. et al., "Dynamic Fluorescence Anisotropy Imaging Microscopy in the Frequency Domain (rFLIM)", Biophysical Journal, vol. 83, Sep. 2002, pp. 1631-1649.
Fixler, D. et al., "Tracing Apoptosis and Stimulation in Individual Cells by Fluorescence Intensity and Anisotropy Decay", Journal of Biomedical Optics, vol. 10, No. 3, May/Jun. 2005, pp. 034007-1 to 034007-8.
Verveer et al.; Global Analysis of Fluorescence Lifetime Imaging Microscopy Data; Biophysical Journal, vol. 78, Apr. 2000; pp. 2127-2137.
Lakowicz et al.; Lifetime-selective fluorescence imaging using an rf phase-sensitive camera; Rev. Sci. Instrum. 62 (7); Jul. 1991; pp. 1727-1734.
Theodorus et al.; Fluorescence lifetime imaging microscopy (FLIM): Spatial resolution of microstructures on the nanosecond time scale; Biophysical Chemistry, 48 (1993); pp. 221-239.
Scully et al.; Application of fluorescence lifetime imaging microscopy to the investigation of intracellular PDT mechanisms; Bioimaging 5 (1997); pp. 9-18.
Carlsson et al.; Simultaneous confocal lifetime imaging of multiple fluorophores using the intensity-modulated multiple-wavelength scanning (IMS) technique; Journal of Microscopy; vol. 191; Pt 2; Aug. 1998; pp. 119-127.
R. Jones et al.; "Fluorescence lifetime imaging using a diode-pumped dl-solid-state laser system", Eleoronics Letters, Feb. 18th, 1999, vol. 35 No. 4, pp.
Elson et al.; "Time-domain fluorescence lifetime imaging applied to biological tissue"; Photochem. Photobiol. Sci., 2004, vol. 3, pp. 795-801.

* cited by examiner

Primary Examiner — Jason Sims
(74) Attorney, Agent, or Firm — IP Delta Plus Inc.

(57) ABSTRACT

There is provided an improved method for enhancing fluorescence images of an object, such as a biological tissue, by selectively eliminating or reducing unwanted fluorescence from fluorophores other than the fluorophore of interest. The method is based on the measurement of the lifetime of fluorophores while preserving information related to the fluorescence intensity of the fluorophore of interest.

10 Claims, 6 Drawing Sheets

(i) Lifetime image for fluorophore 1    (i) Lifetime image for fluorophore 2    (i) Raw intensity image (ii) Fraction image for fluorophore 1    (ii) Fraction image for fluorophore 2    (ii) Fluorescence lifetime image (iii) Processed intensity image for fluorophore 1    (iii) Processed intensity image for fluorophore 2    (iii) Processed intensity image (a)    (b)    (c)

FIG. 5

(i) Raw intensity image (ii) Fluorescence liftime image (iii) Processed intensity image for =0.9~1.05ns (iv) Processed intensity image for =1.7~1.83ns

METHOD FOR IMPROVING FLUORESCENCE IMAGE CONTRAST

CROSS-REFERENCE TO RELATED APPLICATIONS

This application is a continuation-in-part of U.S. application Ser. No. 11/024,826 filed Dec. 30, 2004 and entitled "METHOD FOR IMPROVING FLUORESCENCE IMAGE CONTRAST".

TECHNICAL FIELD

The present invention relates to a method for reducing and/or eliminating unwanted fluorescence signals in optical images based on fluorescence lifetime of fluorophores.

BACKGROUND OF THE INVENTION

The monitoring of pharmacokinetics, genetic, cellular, molecular or other types of events in vivo is of great interest to monitor drug or gene therapy efficacy as well as disease status or progression in small laboratory mammals and in the human body. In this respect, fluorescence imaging, both in vitro and in vivo, has been used extensively to generate anatomical and functional information from within cells and organisms.

Fluorescence imaging of internal parts of animals (including humans) for anatomical or functional purposes often involves the injection of an extrinsic fluorophore, typically chemically coupled with another molecule, that distributes within the animal and accumulates preferentially in cells and organs of interest. Images are then acquired by detecting the fluorescence and mapping the signal relative to the anatomy of the animal. However, the excitation and emission spectra of such extrinsic fluorophores often overlap with those of intrinsic fluorophores such that the fluorescence signal is a combination of the signals from each fluorophore. Furthermore, such studies are often conducted using more than one extrinsic fluorophores which may have overlapping spectra. As a result, fluorescence images often contain undesirable signals that obscure the signal from the fluorophore of interest.

Methods commonly used to attenuate or eliminate unwanted fluorescence signals are based on spectral differences of the fluorescence emission, fluorescence lifetime differences (e.g. FLIM), or frequency domain hardware techniques. All of them have limitations. Methods based on spectral difference are limited to fluorophores having emission spectra that do not significantly overlap thereby allowing acquisition of fluorescence at a non-overlapping wavelength which is specific for a particular fluorophore. Methods based on fluorescence lifetime help distinguish signals from different fluorophores but do not retain the information related to fluorophore intensity and consequently information related to concentration of the fluorophore is lost. Frequency domain hardware techniques require multiple image acquisition at a plurality of phase delays to suppress unwanted fluorescence and are therefore time consuming.

Accordingly, it would be desirable to be provided with a fluorescence imaging method overcoming the above-mentioned deficiencies.

SUMMARY OF THE INVENTION

The present invention provides an improved method for enhancing contrast and specificity of fluorescence images of an object, such as a biological tissue, by selectively eliminating or reducing unwanted fluorescence from fluorophores other than the fluorophore of interest. The method is based on the generation of intensity images weighted as a function of measured lifetime in which the intensity information is conserved and hence information related to the concentration of the fluorophore of interest.

Thus in one embodiment there is provided a method for optical imaging of an object containing two or more fluorophore species in which a fluorescence signal is acquired, using time domain or frequency domain, for one or more region of interest (ROI) of the object using an excitation and an emission wavelength compatible with detection of at least one of the two or more fluorophore species. A fluorescence intensity and a fluorescence lifetime are calculated from the fluorescence signals for each of the pixels and the fluorescence intensity is multiplied by a weighting factor. The weighting factor is a function of the calculated fluorescence lifetime and one or more predetermined fluorescence lifetime of the fluorophore species and is used to generate a weighted fluorescence intensity for each pixel of the ROI from which a weighted fluorescence intensity image can be obtained.

In a further embodiment, the method also provides for an adjustment of the fluorescence intensity to account for the relative contribution of each fluorophore. Thus when the fluorescence signal comprises contribution from two or more fluorophore species a contribution fraction is derived for at least one of the fluorophore species and the weighted fluorescence intensity is multiplied by the contribution fraction. The contribution fraction can be determined, for example, by fitting a temporal point spread function (TPSF) of the fluorescence signal with a sum of exponential decays.

In yet a further embodiment, the method provides for a primary weighting step which can substantially reduce background fluorescence signal from intrinsic fluorophore species. Thus the fluorescence intensity signal can be multiplied by a primary weighting factor prior to the step of multiplying the fluorescence intensity by a weighting factor, the primary weighting factor being a function of the calculated fluorescence lifetime and two predetermined fluorescence lifetimes of two or more fluorophore species that are being imaged.

BRIEF DESCRIPTION OF THE DRAWINGS

Further features and advantages of the present invention will become apparent from the following detailed description, taken in combination with the appended drawings, in which:

FIG. 5(*a-i*) is a raw fluorescence intensity (integration over time of the TPSF in each pixel) image of a [55%:45%] mixture of two fluorophore species namely Cy 5.5 and Atto 680;

FIG. 5(*a-ii*) is an effective lifetime image generated by fitting the fluorescence TPSF from the dual-dye mixture in each pixel with a monoexponential decay model.

FIG. 5(*a-iii*) exhibits a processed intensity image ($I_{new}$) obtained by performing a preliminary weighting on the raw intensity image FIG. 1(*a-i*);

FIG. 5(*b-i*) exhibits a fluorescence lifetime image of Cy5.5 calculated by dual exponential-decay fitting of the fluorescence TPSF of the dual-dye mixture in each pixel;

FIG. 5(*b-ii*) exhibits an intensity fraction image of Cy 5.5 calculated by dual exponential-decay fitting of the fluorescence TPSF of the dual-dye mixture in each pixel;

FIG. 5(*b-iii*) exhibits a weighted fluorescence intensity image ($I^1_w$) of Cy 5.5 obtained by the method of the invention; At each pixel, the fluorescence intensity is related to the concentration of Cy5.5 at that location;

FIG. 5(*c-i*) exhibits a fluorescence lifetime image of Atto680 calculated by dual exponential-decay fitting of the fluorescence TPSF of the dual-dye mixture in each pixel;

FIG. 5(*c-ii*) exhibits an intensity fraction image of Atto680 calculated by dual exponential-decay fitting of the fluorescence TPSF of the dual-dye mixture in each pixel;

FIG. 5(*c-iii*) exhibits a weighted fluorescence intensity image ($I^2_w$) of Atto680 obtained by the method of the invention; At each pixel, the fluorescence intensity is related to the concentration of Atto680 at that location;

FIG. 6(*ii*) is a fluorescence lifetime image of the fluorophores Atto680 and Cy5.5; One can distinguish the two fluorophores by their fluorescence lifetime; This is the mechanism behind the fluorescence lifetime image; However, fluorescence intensity (and thus concentration) information is lost in this image;

FIG. 6(*iii*) is a fluorescence intensity image of Cy5.5 extracted from FIG. 6(*i*) using the method of the invention; and FIG. 6(*iv*) is a fluorescence intensity image of Atto 680 extracted from FIG. 6(*i*) using the method of the invention.

It will be noted that throughout the appended drawings, like features are identified by like reference numerals.

DETAILED DESCRIPTION OF THE PREFERRED EMBODIMENT

Figure 1A:
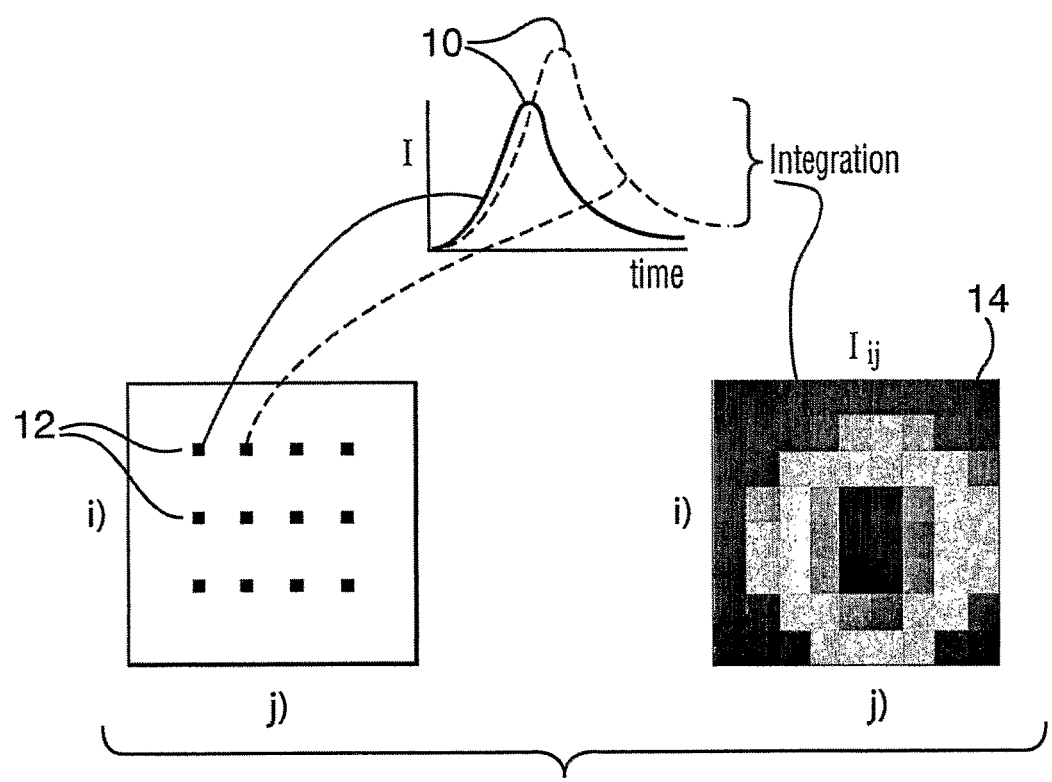
FIG. 1A is a schematic representation of the generation of an intensity image from fluorescence signal from a region of interest (ROI) of an object.

The present invention provides an improved method for enhancing fluorescence images of an object, such as a biological tissue, by selectively eliminating or reducing unwanted fluorescence from fluorophores other than the fluorophore of interest. The method is based on the measurement of the fluorescence intensity and lifetime of fluorophores. The resulting image preserves information related to the fluorescence intensity (and thus the concentration) of the fluorophore of interest. It will be appreciated that the method may be applied to different techniques such as optical imaging, time-resolved fluorescence microscopy and the like.

In the present disclosure by fluorophore species it is meant fluorophores having different fluorescence lifetime. Thus fluorophore species may refer to different fluorescent molecules but it may also refer to the same fluorescent molecule in different environments with each environment conferring the fluorophore a different fluorescence lifetime. For example, conditions such as pH, viscosity, temperature and the like are known to affect the lifetime of fluorophores. The environment may also refer to the molecular environment of the fluorophore. For example a fluorophore that is free typically exhibits a different lifetime than the same fluorophore bound to another molecule. The term fluorophore may refer to small molecules or to macromolecules such as proteins that may comprise molecular electronic configurations capable of emitting fluorescent light when excited.

In one embodiment of the present invention the lifetime of a fluorophore species and intensity of the fluorescence are obtained using time domain (TD) imaging device. A time resolved fluorescence image can be obtained by exciting a fluorophore of interest with a pulsed light source at a fluorescence excitation wavelength and by collecting the fluorescence signal at a fluorescence emission wavelength using a time-resolved photo detector. The pulsed light source can be any type of pulsed laser (e.g. diode laser, solid state laser, gas laser etc.) or other pulsed light sources (e.g. pulsed lamp). The time-resolved photo detector can be, for example, a photo multiplier tube (PMT)/avalanche photodiodes (APD)/PIN coupled with time correlated single photon counting (TCSPC), a streak camera, or a gated intensified charged coupled device (ICCD).

The fluorescence image can be generated by direct imaging of the fluorescent object using a camera or by raster scanning the fluorescent object using a point detector and reconstructing the image using information from each detection point (pixel). An example of the latter modality is employed by the eXplore Optix™ imager described in international patent application WO 2004/044562 A1 which is incorporated herein by reference.

While the embodiments of the invention will be described using time domain as an exemplary modality of data acquisition, it will be appreciated that the method of the invention may also be applied using frequency domain data acquisition. In frequency domain, one can obtain fluorescence intensity and lifetime by measuring the change of modulation depth and the phase shift of fluorescence signal relative to the excitation light signal. Such measurements are well known in the art (Hawrysz and Sevick-Muraca, Neoplasia vol. 2 (5), 2000 p. 388-417 which is incorporated herewith by reference).

Figure 1B:
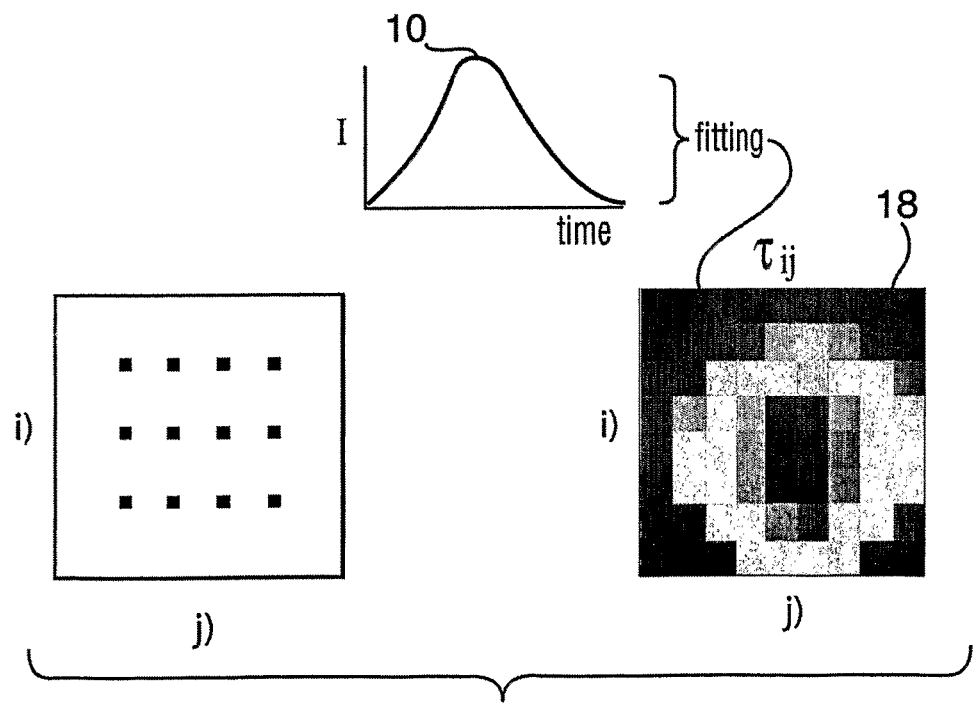
FIG. 1B is a schematic representation of the generation of a lifetime image from fluorescence signal from a region of interest (ROI) of an object.

As shown in FIG. 1A, each signal acquisition corresponds to a temporal point spread function (TPSF, denoted as $l_{ij}(t)$) 10 of the fluorescence signal emitted by the object at a specific detection point 12. By time integrating, either completely or partially, the TPSF at each pixel $l_{ij}(t)$, one can get a CW fluorescence intensity image 14, denoted by $I_{ij}^{CW}$ which can provide information on the concentration. Furthermore, by mathematically fitting $l_{ij}(t)$, one can obtain the fluorescence lifetime which can be used to generate a lifetime image 18, denoted by $\tau_{ij}$ (FIG. 1B). If the fluorescence signal is from more than one fluorophore species, a multi-exponential decay model can be used to fit the $l_{ij}(t)$ and to derive lifetimes for each fluorophore species and contribution fractions of the species.

In most practical cases a TPSF measured at a given point is usually composed of several exponential decays due to the various endogenous and exogenous fluorophore species present in the system. The measured TPSF may then be written as $$I_{ij}(t) = \sum_{k=1}^{n} \alpha_{ij}^{k} \exp(-t/\tau_{ij}^{k})$$ Eq. (1)

where index k represents the $k_{th}$ component (fluorophore species) considered in the n-component analysis, $\alpha_{ij}^{k}$ represents the amplitude of the $k_{th}$ component at t=0. The meaning of the parameter $\alpha_{ij}^{k}$ is different for a mixture of fluorophores than for one fluorophore displaying a complex decay. For the latter case, it is generally safe to assume that $\alpha^{k}$ values represent the fraction of the molecules in each conformation at t=0, which corresponds to the ground state equilibrium.

The meaning of $\alpha^{k}$ is more complex for a mixture of fluorophores. In this case, the relative $\alpha^{k}$ values depend on many factors, i.e. quantum yield, concentration, extinction coefficient, excitation and emission spectra, filter characteristics, system optical components, etc. In general, the fluorescence signal of single fluorophore with monoexponential intensity decay can be written as $$F^k(t) = C^k \cdot \epsilon^k(\lambda) \cdot M^k \cdot Q^k(\lambda) \cdot K^k(\lambda) \cdot S(\lambda) \cdot I_x(\lambda,t) \otimes IRF(t)$$
$$\otimes D(\lambda,t) \otimes \exp(-t/\tau^k)$$ Eq. (2)

In the expression, $C^k$ is molar concentration, $\epsilon^k(\lambda)$ is molar extinction coefficient, $M^k$ is fluorophore dimension, $Q^k(\lambda)$ is quantum yield, $K^k(\lambda)$ is a factor related to the fluorophore excitation and emission spectrum as well as the excitation laser wavelength and the system fluorescence filters, $S(\lambda)$ is a factor related to the instrument, e.g. spectral response, $I_x(\lambda,t)$ is the excitation laser, IRF(t) is the system impulse response function, and $D(\lambda,t)$ is the time delay and amplitude attenuation caused by light diffusion if the fluorophore is in turbid medium, $\otimes$ denotes convolution. Here we assume that the light diffusion and system response are independent of fluorophore, that is true for most applications. The fluorescence signal of a mixture of several fluorophores is $$F(t) = \Sigma F_k(t)$$ Eq. (3)

By comparing equation 3 to equation 1, one can obtain the meaning of $\alpha^k$ $$\alpha^k \propto C^k \cdot \epsilon^k(\lambda) \cdot M^k \cdot Q^k(\lambda) \cdot K^k(\lambda)$$ Eq. (4)

Irrespective of whether the multiexponential decay originates with a single fluorophore or multiple fluorophores, the values of $\alpha_{ij}^{k}$ and $\tau_{ij}^{k}$ can be used to determine the fraction ($f_{ij}^{k,CW}$) contribution of each decay time to the steady-state (CW) intensity $$f_{ij}^{k,CW} = \frac{\alpha_{ij}^{k} \tau_{ij}^{k}}{\sum_k \alpha_{ij}^{k} \tau_{ij}^{k}}$$ Eq. (5)

The fraction contribution ($f_{ij}^{k}$) which is proportional to concentration can be calculated by normalizing $\alpha_{ij}^{k}$ $$f_{ij}^{k} = \frac{\alpha_{ij}^{k}}{\sum_k \alpha_{ij}^{k}}$$ Eq. (6)

Generally, curve fitting methods are required to resolve the measured fluorescent signal into its component constituents. In time domain, by convolving the system Impulse Response Function IRF(t) with the modeled fluorescent decays of the components, a calculated signal $F_c(t)$ is compared to the measured fluorescent signal $F_m(t)$. With the use of numerical curve fitting methods, estimates of the lifetimes and/or relative fractional contribution of each of the n components can be obtained. For example, in least squares analysis, $\alpha_{ij}^{k}$ and $\tau_{ij}^{k}$ are obtained by minimizing the goodness-of-fit parameter $$\chi_R^2 = \frac{1}{\nu} \sum_{l=1}^{L} \frac{1}{\sigma_l^2} [F_m(t_l) - F_c(t_l)]^2$$ Eq. (7)

Where the sum extends over the number (L) of channels or data points, and $\sigma_l$ is the standard deviation of each data point, $\nu$ is the number of degrees of freedom.

In frequency domain, the measurable are phase shift $\phi_\omega$ and modulation depth $m_\omega$ at frequency $\omega$. The calculated values are $$\phi_{c\omega} = \arctan(N_\omega/D_\omega)$$ Eq. (8)

$$m_{c\omega} = \sqrt{N_\omega^2 + D_\omega^2}$$ Eq. (9)

In the expressions, $N_\omega$ and $D_\omega$ are the sine and cosine transform of the fluorescent signal predicted by model. For a simple sum of several exponential decays like equation 1 $N_\omega$ and $D_\omega$ have simple forms $$N_\omega = \sum_k \frac{\alpha^k \omega (\tau^k)^2}{(1+\omega^2(\tau^k)^2)} / \sum_k \alpha^k \tau^k$$ Eq. (10)

$$D_\omega = \sum_k \frac{\alpha^k \tau_k}{(1+\omega^2(\tau^k)^2)} / \sum_k \alpha^k \tau^k$$ Eq. (11)

In least squares data analysis, the parameters ($\alpha_{ij}^{k}$ and $\tau_{ij}^{k}$) are varied to yield the best fit between the data and the calculated values, as indicated by a minimum value for the goodness-of-fit parameter $$\chi_R^2 = \frac{1}{\nu} \sum_\omega \left[\frac{\phi_\omega - \phi_\omega}{\delta\phi}\right]^2 + \frac{1}{\nu} \sum_\omega \left[\frac{m_\omega - m_\omega}{\delta m}\right]^2$$ Eq. (12)

where $\nu$ is the number of degrees of freedom, and $\delta\phi$ and $\delta m$ are the uncertainties in the phase and modulation values, respectively.

Figure 2:
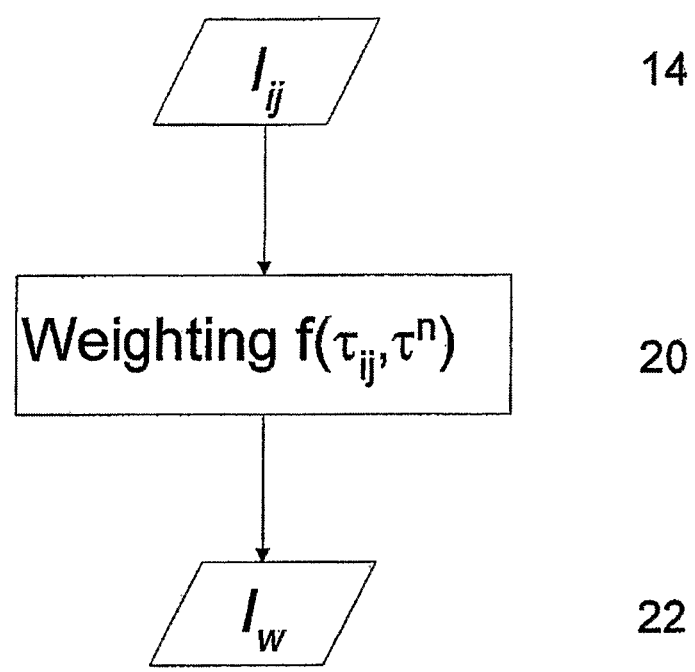
FIG. 2 is a flow chart of an embodiment of the invention in which a weighted intensity image is obtained from a raw intensity image.

Referring to FIG. 2 and assuming that the fluorophore species of interest (i.e. from which the image is to be reconstructed) has a fluorescence lifetime $\tau$, the intensity image 14 can be multiplied at 20 by a weighting factor which is a function of the fluorescence lifetime $\tau$ and the measured (effective) fluorescence lifetime $\tau_{ij}$ used to generate a weighted fluorescence intensity image at 22 which is representative of the distribution and the concentration of the fluorophore species of interest.

In one embodiment, the weighting factor is determined by an Indicator (or Rect) function defined by a range of user determined lifetimes that encompasses the measured lifetime $\tau_{ij}$ at a particular pixel. Pixels exhibiting lifetimes outside the predetermined range can be weighted accordingly or simply eliminated.

In a preferred embodiment the error $\Delta\tau$ derived from the fitting of the TPSF to calculate the effective lifetime can be used to determine the range. Thus one can generate a logical image map $L_{ij}$ by the following criteria:

$$L_{ij} = \begin{cases} 1 & \text{if } \tau - \Delta\tau < \tau_{ij} < \tau + \Delta\tau \\ 0 & \text{otherwise} \end{cases} \quad \text{Eq. (13)}$$

By element-wise multiplying this matrix to the raw intensity image $I_{ij}$, one could get a weighted intensity image $I_w$, in which unwanted fluorescence and/or noise are suppressed. It will be noted that this treatment of the fluorescence signal retains the intensity information of the fluorescence signal.

In the case where two (or more) fluorophore species are contributing to the TPSF, one can obtain the fluorescence lifetimes $\tau_{ij}^1$ and $\tau_{ij}^2$ (more generally $\tau''_{ij}$, and the contribution fractions $f_{ij}^1$ and $f_{ij}^2$ (more generally $f_{ij}^n$) where $f_{ij}^1 + f_{ij}^2 = 1$ of the two fluorophores by fitting the TPSF when using a dual exponential decay model.

Figure 3:
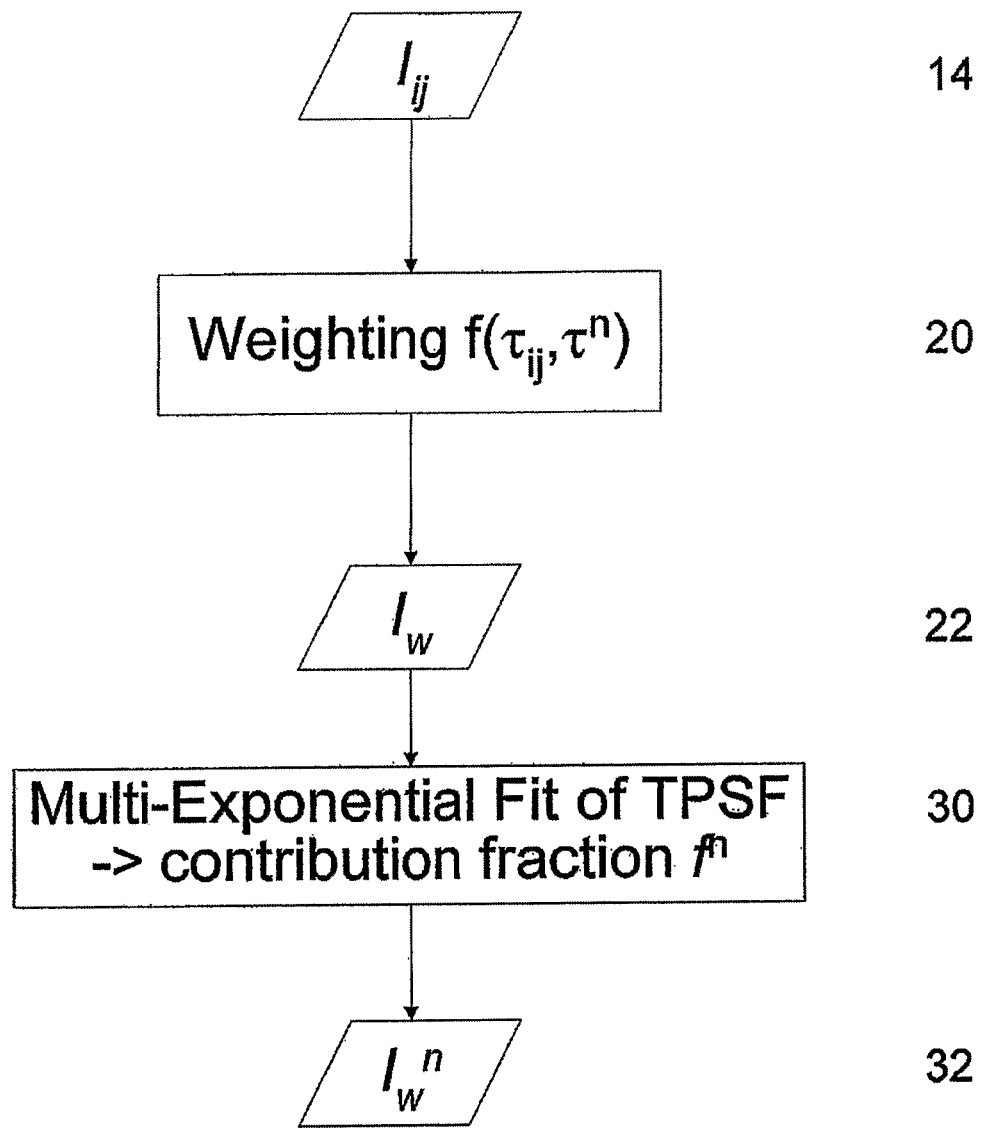
FIG. 3 is a flow chart of an embodiment of the invention in which a contribution fraction adjusted weighted intensity image is obtained from a raw intensity image.

Referring now to FIG. 3, by element-wise multiplying matrix $f_{ij}^n$ to $I_w$ at 30, one can get a new intensity image $I''_w$ at 32, which is proportional to the intensity of fluorophore species n. If only 2 fluorophore species are present image $I^2_w$ can be obtained by the method summarized in FIG. 3 or by simply subtracting $I^1_w$ from $I_w$. It will be appreciated that the contribution fractions can be multiplied to the raw intensity image I before performing the weighting step.

Figure 4:
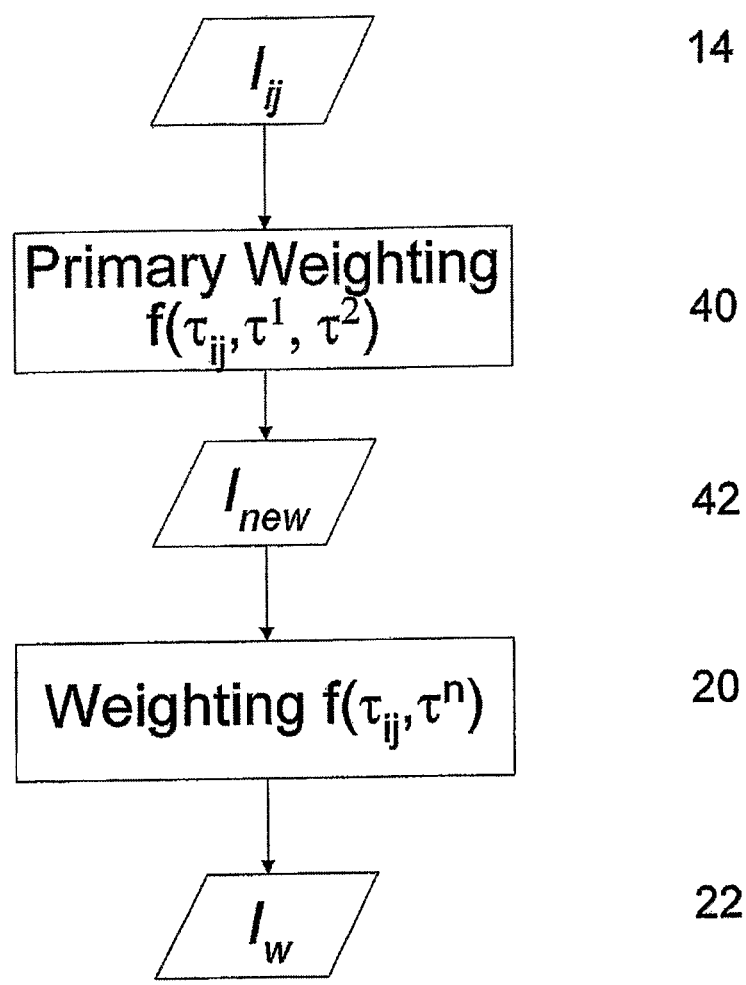
FIG. 4 is a flow chart of an embodiment of the invention in which a primary weighting is applied to the raw intensity image.

Referring now to FIG. 4, it may be advantageous to "clean" the intensity image, prior to weighting, by performing a preliminary weighting at 40 based on the lifetimes of at least two fluorophore species. For example, in an object comprising two fluorophore species with fluorescence lifetimes $\tau_1$ and $\tau_2$, and where $\tau_1 < \tau_2$, then the measured fluorescence lifetime $\tau$ satisfies $\tau_1 < \tau < \tau_2$ if a single exponential decay model is used. Further assuming the fitting error is $\Delta\tau$, then one can generate a logical image map by the following criteria $$L_{ij} = \begin{cases} 1 & \text{if } \tau_1 - \Delta\tau < \tau_{ij} < \tau_2 + \Delta\tau \\ 0 & \text{otherwise} \end{cases} \quad \text{Eq. (14)}$$

By element-wise multiplying this matrix to the intensity image $I_{ij}$, one can generate a new intensity image $I_{new}$ at 42 which is background suppressed. The background may comprise, for example, fluorescence from intrinsic molecules. $I_{new}$ can then be used in the process described in FIGS. 2 and 3 to obtain $I_w$, $I^1_w$, etc.

It will be appreciated that the method described above can be extended to multi-fluorophore species using a multi-exponential decay model for fluorescence lifetime fitting instead of dual exponential decay model.

It will also be appreciated that the ranges of lifetime on which the weighting is based can be defined by the user according to the desired fluorescence information. In a preferred embodiment, the ranges are defined by the expected ($\tau''$) lifetime of the fluorophore species.

For applications such as diagnosis and pharmacological studies, it is often desirable to have an image that provides information on the concentration and depth of the fluorophore species. However, to simply assume that the fluorescence intensity signal is proportional to the flurophore concentration can be misleading since the depth, lifetime, fluorescence spectrum of the flurophore and characteristics of the instrument, as well as light diffusion of tissue will also impact the fluorescence intensity signal. Thus to generate an image that reflects the concentration of the fluorophore species all these factors and the propagation loss of the fluorescence due to tissue absorption and scattering should be taken in consideration. An example of concentration determination is provided below.

EXAMPLES

Example 1

Equal volumes of 50 nM Cy5.5 and 150 nM Atto680 were mixed together. Fluorescence signal was obtained using eXplore Optix™ with a pulsed diode laser wavelength at 666 nm as the excitation light source. When the quantum yield, extinction coefficient, and fluorescence spectrum and filter window information are taken into account, the fluorescence signal ratio of Cy5.5 and Atto680 from the mixture is about 0.55:0.45.

FIG. 5 illustrates the method described above. Panel (a-i) is a raw fluorescence intensity image of the Cy 5.5 and Atto 680 mixture. A lifetime image (panel (a-ii)) was generated using an effective lifetime (fitting the TPSF with a single exponential). Panel (a-iii) exhibits a processed intensity image ($I_{new}$) obtained by performing a preliminary weighting on the raw intensity image. Because only Cy5.5 and Atto 680 are present there is no difference between the raw image and processed image (no background fluorescence). Panels (b-i) and (c-i) exhibit lifetime images based on the lifetime of one fluorophore species only after dual exponential fitting of the TPSF. Panels (b-ii) and (c-ii) exhibit a contribution factor image of the fluorophore species. Both lifetime and fraction are obtained at the same time by direct fitting of the TPSF in each pixel using a dual exponential decay model. Panels (b-iii) and (c-iii) exhibit a weighted fluorescence intensity image ($I^1_w, I^2_w$) obtained by the method described above. In the present example the fluorescence intensity is proportional to the concentration of Cy5.5 or Atto680 since both fluorophore are at the same depth (phantom surface) and other factors are taken into account.

Example 2

One hundred nM Cy5.5 and 200 nM Atto680 solution were arranged in two separate locations. Fluorescence signal was obtained using eXplore Optix with a pulsed diode laser wavelength at 666 nm as the excitation light source.

Figure 6:
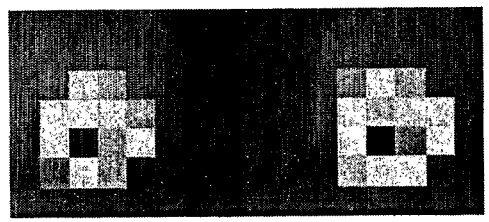
FIG. 6(*i*) is a raw fluorescence intensity (integration over time of the TPSF in each pixel) image of Cy 5.5 and Atto680; On the left is Atto680; On the right is Cy5.5; One can not distinguish the fluorescence by fluorescence intensity only.
Figure 6:
Figure 6:
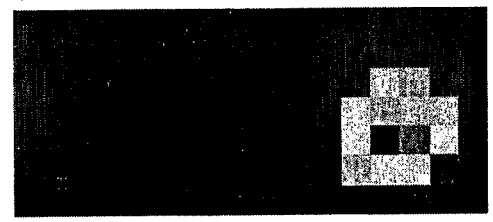
Figure 6:
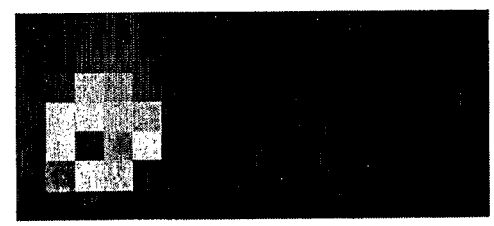

In the particular case where the location of fluorophore species within the object are not overlapping, there is no need for multi-exponential fitting of the TPSF and one can proceed directly with the weighting step of the method. FIG. 6 provides such an example in which the two fluorophores species do not overlap. Panel (i) of FIG. 6 is a measured raw fluorescence intensity image with two fluorophore species, Atto 680 on the left and Cy5.5 on the right. From the intensity image alone, without knowing a priori where the fluorophores are located, one would not be able to identify the fluorophores species. Panel (ii) is the corresponding fluorescence lifetime image obtained by fitting the TPSF of each pixel with a single exponential decay model. While the lifetime image enables the determination of the species of the fluorophore if the lifetimes are known a priori, it does not convey any intensity information. However, when the method of the present invention is used the intensity information is preserved. Thus in the example provided below the weighting function was based on a range of lifetimes determined to be between 0.9 and 1.05 ns for Cy 5.5 and 1.7 and 1.83 ns for Atto 680. Using the criteria:

$$L_{ij} = \begin{cases} 1 & \text{if } 0.9 < \tau_{ij} < 1.05 \\ 0 & \text{otherwise} \end{cases}$$

for Cy 5.5 one obtains the image displayed in panel (iii) and $$L_{ij} = \begin{cases} 1 & \text{if } 1.7 < \tau_{ij} < 1.83 \\ 0 & \text{otherwise} \end{cases}$$

for Atto 680 one obtains the image displayed in panel (iv). Both images retain the intensity information for the fluorophore of interest. Since they are both at the same depth (phantom surface) and have the same dimension, the intensity is related to their concentration through lifetime quantum yield, extinction coefficient, fluorescent spectrum, filter window, and other known instrument parameters.

Example 3

The fluorophore species may be the same fluorophore molecule in different environment. Thus, for example, the object may comprise one fluorophore having a lifetime $\tau_1$ when it is bound to a protein and a lifetime $\tau_2$ when it is free. In this case it is possible to model the TPSF by the following dual exponential:

$$f \exp(-t/\tau_1) + (1-f)\exp(-t/\tau_2) \quad (15)$$

where, t is the time, $\tau_1$ and $\tau_2$ are the respective lifetimes of the bound and free states and f is the fraction of fluorophores in the bound state: f=[bound]/([bound]+[free]). The parameters in this model can then be obtained from measured data through multi-variate curve fitting. The dual exponential for free/bound fluorophore species can be used to obtain weighted intensity images as described above.

Example 4

Under certain assumptions such as assuming that the optical properties of the medium are the same at the excitation and emission wavelength, the fluorescence intensity as a function of time can be expressed by the Born approximation:

$$\phi(t) \cong \qquad (16)$$

$$\sum_{dipoles} \left( QC \frac{r_{sp} + r_{pd}}{4\pi D r_{sp} r_{pd}} v(4\pi D v t)^{-3/2} e^{-\frac{(r_{sp}+r_{pd})^2}{4Dvt} - \mu_a v t} \right) * \left( \frac{e^{-\frac{t}{\tau}}}{\tau} \right) * (IRF)$$

Where:
$r_{sp}$ is the distance from source s (point on the object at which light is injected) to fluorophore depth position p;
$r_{pd}$ is the distance from fluorophore depth position p to detector d;
$\mu_a$ is the optical absorption coefficient;
D is the optical diffusion coefficient, $$D = \frac{1}{3\mu_s'}$$

where; $\mu_{s'}$ is the reduced optical scatter coefficient;
v is the speed of light in the medium;
Q is the quantum efficiency;
C is the concentration of the fluorophore;
$\tau$ is the lifetime of the fluorophore;
the symbol * refers to the operation of convolution and IRF is the impulse response function of the instrument used to measure fluorescence.

By setting the first derivative of equation 6 as a function of time equal to zero, the time position of the maximum of the TPSF ($t_{max}$) can be found. Under certain approximations (absorption is small at time shorter than $t_{max}$, the scatter coefficient is known or can be approximated) and by assuming that $r_{sp}$ is approximately equal to $r_{pd}$, it is found that the following equation can be derived from equation 16:

$$t_{max} \cong \frac{d\sqrt{\tau}}{\sqrt{Dv}} \qquad (17)$$

where d is the depth of the fluorophore object.

For a given depth, the intensity I of the emission signal detected at the surface can be related to fluorophore concentration by the optical properties of the medium (absorption and scattering coefficients) and the depth of the fluorophore.

$$I \propto Ce^{-\sqrt{\frac{\mu_a}{D}}d} \qquad (18)$$

Using time-domain information as described above, the depth d can be determined. Isolating C in equation 8 and knowing signal intensity and depth of the fluorophore, one can thus recover the concentration of fluorophore (i.e. the amount of fluorescent molecules per unit volume) within an accuracy that depends exponentially on the recovered depth accuracy. Thus, in another aspect of the invention, estimates of the relative concentration of the fluorophore, $Conc._{relative}$, can be obtained by determining its depth, d, and normalizing the surface intensity measurement, I, as follows (Equation 9):

$$Conc._{Relative} = Id^2 e^{2d\sqrt{\mu_a/D}} \qquad (19)$$

under certain assumptions, equation 19 can be derived from equation 16.

If the fluorophore objects are not at the surface of the tissue, the method described above can be used to obtain their concentration map from the weighted intensity image.

The embodiment(s) of the invention described above is (are) intended to be exemplary only. The scope of the invention is therefore intended to be limited solely by the scope of the appended claims.

I claim:
1. A method for improving optical imaging fluorescence contrast of a region of interest (ROI) of an object containing two or more fluorophore species, said method comprising:
exciting the fluorophore species with a pulsed light source at a fluorescence excitation wavelength;
collecting by a time-resolved photo detector temporal point spread function of the (ROI) of the object, temporal point spread function comprising time and ampli- tude information for a plurality of pixels wherein each pixel corresponds to a detection point of the time-resolved photo detector;

generating by a computer a Continuous Wave fluorescence intensity image by performing a time integration of the collected temporal point spread function of the fluorescence signal for each pixel;

improving, by the computer, contrast of each of the plurality of pixels of the Continuous Wave fluorescence intensity image by multiplying the Continuous Wave fluorescence intensity of each pixel by a weighting factor, the weighting factor being representative of a fraction contribution of each fluorophore decay time to the Continuous Wave fluorescence intensity image, the weighting factor being calculated by:

$$f_{ij}^{k,CW} = \frac{\alpha_{ij}^k \tau_{ij}^k}{\sum_k \alpha_{ij}^k \tau_{ij}^k}$$

where: i,j represents each pixel;
k is an index of the fluorophore species;
$\alpha_{ij}^k$ represents an amplitude of a $k_{th}$ fluorophore; and
$\tau_{ij}^k$ represents a fluorescence lifetime of the $k_{th}$ fluorophore; and generating, using the computer, an optical image using the plurality of pixels with improved contrast.

2. The method as claimed in claim 1 further comprising:
deriving by the computer a contribution fraction for at least one of said fluorophore species for each of the pixels; and
multiplying by the computer said weighted fluorescence intensity by said contribution fraction for each of the pixels.

3. The method as claimed in claim 2 wherein said contribution fraction is determined by modeling said fluorescence signal with a multi-exponential decay function by the computer.

4. The method as claimed in claim 1 wherein said Indicator function for each pixel is defined by boundaries which are function of said at least one predetermined fluorescence lifetime.

5. The method as claimed in claim 4 wherein said boundaries are also function of an error associated with said calculated fluorescence lifetime.

6. The method as claimed in claim 2 further comprising a step of:
multiplying by the computer said fluorescence intensity of each pixel by a preliminary weighting factor prior to multiplying said fluorescence intensity by said weighting factor or said contribution fraction, whereby said preliminary weighting factor being an Indicator function of said calculated fluorescence lifetime and two predetermined fluorescence lifetimes corresponding to expected lifetimes of said two or more fluorophore species.

7. The method as claimed in any one of claims 1-3, 4-5 and 6 wherein said fluorescence species comprises a fluorophore that is distributed between a free state and a bound state.

8. The method as claimed in any one of claims 1-3, 4-5 and 6 wherein said weighted intensity is further processed to yield concentration of at least one of said two or more fluorophore species.

9. The method as claimed in claim 4 wherein said predetermined fluorescence lifetime consists of two predetermined fluorescence lifetimes, said boundaries are the two predetermined fluorescence lifetimes, and the Indicator function for said pixel is 1 when said calculated fluorescence lifetime is within said boundaries, and 0 when said calculated fluorescence lifetime is outside said boundaries.

10. The method as claimed in claim 5 wherein said fluorescence signal comprises contribution from two or more fluorophore species, the at least one predetermined fluorescence lifetime corresponds to the contribution of a specific fluorophore among the two or more fluorophore species, the error is associated to the calculated fluorescence lifetime of the specific fluorophore, and the boundaries are respectively the predetermined fluorescence lifetime corresponding to the contribution of the specific fluorophore minus the error and the predetermined fluorescence lifetime corresponding to the contribution of the specific fluorophore plus the error, and the Indicator function is 1 when said calculated fluorescence lifetime is within said boundaries, and 0 when said calculated fluorescence lifetime is outside said boundaries.

* * * * *